(12) United States Patent
Parkot et al.

(10) Patent No.: US 9,441,211 B2
(45) Date of Patent: Sep. 13, 2016

(54) FUCOSYLTRANSFERASES AND THEIR APPLICATIONS

(71) Applicant: Jennewein Biotechnologie GmbH, Rheinbreitbach (DE)

(72) Inventors: Julia Parkot, Köln (DE); Eric Hüfner, Hennef (DE); Stefan Jennewein, Aachen (DE)

(73) Assignee: JENNEWEIN BIOTECHNOLOGIE GMBH, Rheinbreitbach (DE)

(*) Notice: Subject to any disclaimer, the term of this patent is extended or adjusted under 35 U.S.C. 154(b) by 0 days.

(21) Appl. No.: 13/860,452

(22) Filed: Apr. 10, 2013

(65) Prior Publication Data

US 2013/0217068 A1    Aug. 22, 2013

Related U.S. Application Data

(63) Continuation of application No. PCT/EP2011/067538, filed on Oct. 7, 2011.

(30) Foreign Application Priority Data

Oct. 11, 2010 (EP) ..................... 10187167

(51) Int. Cl.
| | | |
|---|---|---|
| C12N 9/10 | (2006.01) | |
| C12P 19/18 | (2006.01) | |
| C12P 21/00 | (2006.01) | |
| C12P 19/44 | (2006.01) | |

(52) U.S. Cl.
CPC ............. *C12N 9/1051* (2013.01); *C12P 19/18* (2013.01); *C12P 19/44* (2013.01); *C12P 21/005* (2013.01); *C12Y 204/01214* (2013.01); *Y02P 20/52* (2015.11)

(58) Field of Classification Search
None
See application file for complete search history.

(56) References Cited

U.S. PATENT DOCUMENTS

| 5,922,577 A | 7/1999 | Defrees et al. |
| 6,534,928 B1 | 3/2003 | Li et al. |
| 2006/0234354 A1 | 10/2006 | Sjoberg |

FOREIGN PATENT DOCUMENTS

| JP | 1995-313166 | 12/1995 |
| JP | 1999-503329 | 3/1999 |
| JP | 2003-510330 | 4/2001 |
| JP | 2004-512002 | 4/2004 |
| JP | 2008-507297 | 3/2006 |
| JP | 2007-520220 | 7/2007 |
| JP | 2009-095264 | 5/2009 |
| JP | 2009-523420 | 6/2009 |
| JP | 2010-5147698 | 6/2010 |
| WO | WO 96/32491 | 10/1996 |
| WO | WO 98/55630 | 12/1998 |
| WO | WO 99/36555 | 7/1999 |
| WO | WO 00/49153 | 8/2000 |
| WO | WO 01/23398 | 4/2001 |
| WO | WO 2005/69921 | 8/2005 |
| WO | WO 2006/015165 | 2/2006 |
| WO | WO 2007/084342 | 7/2007 |
| WO | WO 2008/143713 | 11/2008 |

OTHER PUBLICATIONS

Dumon et al., Biotechnol Prog, 2004, vol. 20, pp. 412-419.*
Comstock et al., Cell, 2006, vol. 126 pp. 847-850.*
Kuwahara et al. "Genomic Analysis of *Bacteroides fragilis* Reveals Extensive DNA Inversions Regulating Cell Surface Adaption," *PNAS* 101(41):14919-14924 (2004).
Cerdeno-Tarraga et al. "Extensive DNA Inversions in the *B. fragilis* Genome Control Variable Gene Expression," *Science* 307:1463-1465 (2005).
Database EMBL: *Bacteroides fragilis* YCH46 DNA, complete genome, EBI accession No. EMBL: AP006841 (2004).
Database EMBL *Bacteroides fragilis* NCTC 9343, complete genome, EBI accession No. EM_PRO: CR626927 (2005).
Database EMBL: *Akkermansia muciniphila* ATCC BAA-835, complete genome, EBI accession No. EMBL: CP001071 (2008).
International Preliminary Report on Patentability dated Apr. 12, 2013, from PCT/EP2011/067538.
Weston et al., "Isolation of a Novel Human α(1,3)Fucosyltransferase Gene and Molecular Comparison to the Human Lewis Blood Group α(1,3/1,4)Fucosyltransferase Gene," *Journal of Biological Chemistry* 27(6):4152-4160 (Feb. 25, 1992).
NCBI Accession No. AP_001877377, "Hypothetical protein Amuc_0760 [Akkermanasia muciniphila ATCC BAA-835]," (Jun. 10, 2013).
Genbank® Accession No. ACD04596.1, 1 page (May 8, 2008).
Genbank® Accession No. BAD50785.1, 1 page (Jan. 18, 2008).
Genbank® Accession No. BAI71347, 2 Pages (Dec. 22, 2010).
Genbank® Accession No. CAH09151.1, 1 page (May 13, 2009).

* cited by examiner

*Primary Examiner* — Michele K Joike
*Assistant Examiner* — Mindy G Brown
(74) *Attorney, Agent, or Firm* — Klarquist Sparkman, LLP

(57) ABSTRACT

The present invention relates to nucleic acid and amino acid sequences from *Akkermansia muciniphila* and from *Bacteroides fragilis*, coding for/representing novel alpha-1,3-fucosyltransferases. The invention also provides uses and methods for using the alpha-1,3-fucosyltransferases to generate fucosylated products, such as oligosaccharides, (glyco) proteins, or (glyco)lipids, in particular of 3-fucosyllactose.

18 Claims, 10 Drawing Sheets

Sequence of gene *amuc0760co*:

ATGAAAACGCTGAAAATTAGCTTTCTGCAAAGCACCCCGGATTTCGGCCGTGAGGGTATGCTGCAACTGCTGA
AATCTCGCTATCATGTGGTTGAAGATGATAGTGATTTTGATTACCTGGTGGCGACGCCGTGGTTCTATGTTAAC
CGTGAAGCCTTTTACGATTTCCTGGAACGCGCACCGGGCCATATTACCGTGATGTATGGTTGCCACGAAGCGA
TCGCCCCGGATTTTATGCTGTTCGATTATTACATTGGCCTGGACACCGTGCCGGGTAGCGATCGTACCGTTAAA
CTGCCGTATCTGCGCCATCACCTGGAAGAAGTTCATGGCGGTAAAGAAGGCCTGGATGCACATGCCCTGCTGG
CCAGCAAAACGGGTTTTTGTAACTTCATCTACGCCAATCGTAAATCTCATCCGAACCGCGATGCAATGTTTCAC
AAACTGAGTGCGTTTCGTTTCGTGAATAGCCTGGGCCCGCATCTGAACAATACCCCGGGCGATGGTCACCGTG
CGGAAGATTGGTATGCCAGCTCTATTCGCATGAAAAAACCGTACAAATTTTCTATCGCCTTCGAAAACGCATGG
TACCCGGGTTACACCAGCGAAAAAATCGTTACGTCTATGCTGGCCGGCACCATTCCGATCTATTGGGGTAATCC
GGATATTAGCCGTGAATTTAACAGTGCGAGCTTTATCAATTGCCATGATTTTCCGACGCTGGATGATGCGGCG
GCGTATGTGAAAAAAGTTGATGAAGATGATAACCTGTGGTGTGAAATTATGAGCCGCCCGTGGAAAACCCCG
GAACAGGAAGCACGTTTTCTGGAAGAAACCGAACGCGAAACGGCGAAACTGTATAAAATCTTCGATCAGAGT
CCGGAAGAAGCCCGTCGCAAAGGCGATGGTACCTGGGTGAGCTATTACCAGCGTTTTCTGAAACGTGGTCATC
GTATGCAGCTGGCCTGGCGTCGCCTGAAAAATCGCCTGCGTCGCTAA

Sequence of protein Amuc0760co:

MKTLKISFLQSTPDFGREGMLQLLKSRYHVVEDDSDFDYLVATPWFYVNREAFYDFLERAPGHITVMYGCHEAIAP
DFMLFDYYIGLDTVPGSDRTVKLPYLRHHLEEVHGGKEGLDAHALLASKTGFCNFIYANRKSHPNRDAMFHKLSAFR
FVNSLGPHLNNTPGDGHRAEDWYASSIRMKKPYKFSIAFENAWYPGYTSEKIVTSMLAGTIPIYWGNPDISREFNSA
SFINCHDFPTLDDAAAYVKKVDEDDNLWCEIMSRPWKTPEQEARFLEETERETAKLYKIFDQSPEEARRKGDGTWV
SYYQRFLKRGHRMQLAWRRLKNRLRR

Fig. 5

Sequence of gene *fucT6*:

ATGTGTGATTGCTTGTCTATCATATTGTTAGTCAAAATGAAAAGATTTATTTGAAATTTGTTGATTTTTGGGAT
GGATTTGATACTATTTCTAACTTTATTGTGGATGCTTTGTCCATTCAATACGAAGTAGTACTATCTAATGAGCCA
GATTATTTATTCTATTCATGTTTTGGAACGTCACATTTAGAATATGATTGTATAAAAATCATGTTTATAGGTGAA
AATATAGTTCCTGATTTTAACGTTTGTGATTATGCCATAGGTTTTAATTATATTGATTTTGGGGACCGTTACTTG
AGGTTGCCTTTATATGCTATATATGATGGATTTTCAAACTTGCAGAATAAAAAGATTGATGTAAATAAAGCTTT
AGACCGTAAATTTTGTAGTATTGTTGTTTCAAATAATAAATGGGCAGATCCTATTCGTGAGACTTTCTTTAAATT
ACTATCTAGTTATAAGAAAGTAGACTCTGGTGGAAGAGCTTGGAATAATATAGGAGGACCTGTTGATAATAAA
TTGGATTTTATTAGCCAATATAAGTTTAATATTGCTTTTGAAAATAGTAGGGTACTGGGATATACAACAGAAAA
AATAATGGAACCTATGCAGGTGAATTCTATTCCAGTATATTGGGGAAATCCTTTGGTTGGTAAAGATTTTAATG
TGGACTCCTTTGTAAATGCTCATGATTTTGATTCTTTAGAAAGATTAGTTGAGTATATTATAGAATTGGATTCTT
CAAAGGATAAATATCTGGAAATGTTGGAAAAACCTTGGCTTCTCGATAAGACATATTTGGATTGGAAACAATT
GCTGTTAAATTTTATTAATAATATTATGATGAAATCATATAAGGATGCGAAGTATTTGGTTAATTATGGTCATGC
TGGAAAGTATAGAAATGAACAACGCTTTTGGGGGAGATGTGAACGTAAATTTAAACTTCAAAGAATTATTGAA
TATTATTCTCAATTGTTTGATAGAAAATAA

Sequence of protein FucT6:

MCDCLSIILLVKMKKIYLKFVDFWDGFDTISNFIVDALSIQYEVVLSNEPDYLFYSCFGTSHLEYDCIKIMFIGENIVPDF
NVCDYAIGFNYIDFGDRYLRLPLYAIYDGFSNLQNKKIDVNKALDRKFCSIVVSNNKWADPIRETFFKLLSSYKKVDSG
GRAWNNIGGPVDNKLDFISQYKFNIAFENSRVLGYTTEKIMEPMQVNSIPVYWGNPLVGKDFNVDSFVNAHDFDS
LERLVEYIIELDSSKDKYLEMLEKPWLLDKTYLDWKQLLLNFINNIMMKSYKDAKYLVNYGHAGKYRNEQRFWGRC
ERKFKLQRIIEYYSQLFDRK

Fig. 6

Sequence of gene *fucT7*:

ATGGATATATTGATTCTTTTTTATAATACGATGTGGGGATTTCCACTCGAGTTCCGAAAGGAAGATTTACCTGG
GGGCTGTGTGATAACGACTGATCGAAACCTCATTGCAAAGGCGGATGCTGTGGTTTTCCATTTGCCCGATTTGC
CTTCGGTGATGGAGGATGAAATCGATAAGCGGGAAGGACAGCTTTGGGTGGGATGGAGTCTGGAATGTGAA
GAGAATTATAGTTGGACGAAGGATCCCGAGTTCAGAGAGAGTTTTGACTTATGGATGGGGTATCATCAGGAG
GATGATATTGTGTATCCTTATTATGGACCGGATTATGGGAAGATGCTGGTTACGGCACGGAGGGAAAAGCCTT
ATAAGAAGAAGGCATGTATGTTTATTTCGAGTGATATGAACCGGAGTCATCGACAAGAGTATCTTAAGGAATT
GATGCAGTATACCGACATCGATTCGTATGGGAAACTATACCGTAATTGTGAATTACCTGTTGAGGATCGGGGA
CGGGATACACTTCTTAGTGTGATCGGGGATTATCAGTTTGTGATAAGTTTTGAGAATGCGATAGGGAAGGATT
ATGTGACAGAAAAGTTTTTCAATCCTTTGTTGGCCGGTACTGTTCCGGTCTATCTGGGAGCTCCCAATATTCGG
GAATTTGCTCCGGGAGAAAATTGTTTTCTGGATATTTGTACTTTCGATTCTCCCGAGGGAGTAGCCGCTTTTAT
GAATCAATGCTATGATGACGAGGCATTGTATGAACGTTTTTATGCATGGAGGAAACGGCCTTTATTATTGTCGT
TTACAAAAAAGTTAGAGCAAGTCCGGAGCAATCCGTTAATCAGGCTTTGCCAAAAAATACACGAACTAAAATT
GGGAGGGATATGA

Sequence of protein FucT7:

MDILILFYNTMWGFPLEFRKEDLPGGCVITTDRNLIAKADAVVFHLPDLPSVMEDEIDKREGQLWVGWSLECEENY
SWTKDPEFRESFDLWMGYHQEDDIVYPYYGPDYGKMLVTARREKPYKKKACMFISSDMNRSHRQEYLKELMQYT
DIDSYGKLYRNCELPVEDRGRDTLLSVIGDYQFVISFENAIGKDYVTEKFFNPLLAGTVPVYLGAPNIREFAPGENCFL
DICTFDSPEGVAAFMNQCYDDEALYERFYAWRKRPLLLSFTKKLEQVRSNPLIRLCQKIHELKLGGI

Fig. 7

```
SEQUENCE LISTING

<160> NUMBER OF SEQ ID NOS: 22

<210> SEQ ID NO 1
<211> LENGTH: 999
<212> TYPE: DNA
<213> ORGANISM: Akkermansia muciniphila

<400> SEQUENCE: 1
atgaaaacgc tgaaaattag ctttctgcaa agcacccggg atttcggccg tgagggtatg      60
ctgcaactgc tgaaatctcg ctatcatgtg gttgaagatg atagtgattt tgattacctg     120
gtggcgacgc cgtggttcta tgttaaccgt gaagcctttt acgatttcct ggaacgcgca     180
ccgggccata ttaccgtgat gtatggttgc cacgaagcga tcgccccgga ttttatgctg     240
ttcgattatt acattggcct ggacaccgtg ccgggtagcg atcgtaccgt taaactgccg     300
tatctgcgcc atcacctgga agaagttcat ggcggtaaag aaggcctgga tgcacatgcc     360
ctgctggcca gcaaaacggg ttttgtaac ttcatctacg ccaatcgtaa atctcatccg     420
aaccgcgatg caatgtttca caaactgagt gcgtttcgtt tcgtgaatag cctgggcccg     480
catctgaaca ataccccggg cgatggtcac cgtgcggaag attggtatgc cagctctatt     540
cgcatgaaaa aaccgtacaa attttctatc gccttcgaaa acgcatggta cccgggttac     600
accagcgaaa aaatcgttac gtctatgctg gccggcacca ttccgatcta ttggggtaat     660
ccggatatta gccgtgaatt taacagtgcg agctttatca attgccatga ttttccgacg     720
ctggatgatg cggcggcgta tgtgaaaaaa gttgatgaag atgataacct gtggtgtgaa     780
attatgagcc gcccgtggaa aacccggaa caggaagcac gttttctgga agaaaccgaa     840
cgcgaaacgg cgaaactgta taaaatcttc gatcagagtc cggaagaagc ccgtcgcaaa     900
ggcgatggta cctgggtgag ctattaccag cgttttctga aacgtggtca tcgtatgcag     960
ctggcctggc gtcgcctgaa aaatcgcctg cgtcgctaa                            999
```

<210> SEQ ID NO 2
<211> LENGTH: 332
<212> TYPE: PRT
<213> ORGANISM: Akkermansia muciniphila

<400> SEQUENCE: 2

Met Lys Thr Leu Lys Ile Ser Phe Leu Gln Ser Thr Pro Asp Phe Gly
1               5                   10                  15

Arg Glu Gly Met Leu Gln Leu Leu Lys Ser Arg Tyr His Val Val Glu
            20                  25                  30

Asp Asp Ser Asp Phe Asp Tyr Leu Val Ala Thr Pro Trp Phe Tyr Val
        35                  40                  45

Asn Arg Glu Ala Phe Tyr Asp Phe Leu Glu Arg Ala Pro Gly His Ile
    50                  55                  60

Thr Val Met Tyr Gly Cys His Glu Ala Ile Ala Pro Asp Phe Met Leu
65                  70                  75                  80

Phe Asp Tyr Tyr Ile Gly Leu Asp Thr Val Pro Gly Ser Asp Arg Thr
                85                  90                  95

Val Lys Leu Pro Tyr Leu Arg His His Leu Glu Glu Val His Gly Gly
            100                 105                 110

Lys Glu Gly Leu Asp Ala His Ala Leu Leu Ala Ser Lys Thr Gly Phe
        115                 120                 125

Cys Asn Phe Ile Tyr Ala Asn Arg Lys Ser His Pro Asn Arg Asp Ala
    130                 135                 140

Met Phe His Lys Leu Ser Ala Phe Arg Phe Val Asn Ser Leu Gly Pro
145                 150                 155                 160

His Leu Asn Asn Thr Pro Gly Asp Gly His Arg Ala Glu Asp Trp Tyr
                165                 170                 175

Ala Ser Ser Ile Arg Met Lys Lys Pro Tyr Lys Phe Ser Ile Ala Phe
            180                 185                 190

Glu Asn Ala Trp Tyr Pro Gly Tyr Thr Ser Glu Lys Ile Val Thr Ser
        195                 200                 205

Met Leu Ala Gly Thr Ile Pro Ile Tyr Trp Gly Asn Pro Asp Ile Ser
    210                 215                 220

Arg Glu Phe Asn Ser Ala Ser Phe Ile Asn Cys His Asp Phe Pro Thr
225                 230                 235                 240

Leu Asp Asp Ala Ala Ala Tyr Val Lys Lys Val Asp Glu Asp Asp Asn
                245                 250                 255

Leu Trp Cys Glu Ile Met Ser Arg Pro Trp Lys Thr Pro Glu Gln Glu
            260                 265                 270

Ala Arg Phe Leu Glu Glu Thr Glu Arg Glu Thr Ala Lys Leu Tyr Lys
        275                 280                 285

Ile Phe Asp Gln Ser Pro Glu Glu Ala Arg Arg Lys Gly Asp Gly Thr
    290                 295                 300

Trp Val Ser Tyr Tyr Gln Arg Phe Leu Lys Arg Gly His Arg Met Gln
305                 310                 315                 320

Leu Ala Trp Arg Arg Leu Lys Asn Arg Leu Arg Arg
                325                 330

<210> SEQ ID NO 3
<211> LENGTH: 996
<212> TYPE: DNA
<213> ORGANISM: Bacteroides fragilis

<400> SEQUENCE: 3

```
atgtgtgatt gcttgtctat catattgtta gtcaaaatga aaaagattta tttgaaattt      60
gttgattttt gggatggatt tgatactatt tctaacttta ttgtggatgc tttgtccatt     120
caatacgaag tagtactatc taatgagcca gattatttat tctattcatg ttttggaacg     180
tcacatttag aatatgattg tataaaaatc atgtttatag gtgaaaatat agttcctgat     240
tttaacgttt gtgattatgc cataggtttt aattatattg attttgggga ccgttacttg     300
aggttgcctt tatatgctat atatgatgga ttttcaaact tgcagaataa aaagattgat     360
gtaaataaag ctttagaccg taaattttgt agtattgttg tttcaaataa taaatgggca     420
gatcctattc gtgagacttt ctttaaatta ctatctagtt ataagaaagt agactctggt     480
ggaagagctt ggaataatat aggaggacct gttgataata aattggattt tattagccaa     540
tataagttta atattgcttt tgaaaatagt agggtactgg gatatacaac agaaaaaata     600
atggaaccta tgcaggtgaa ttctattcca gtatattggg aaatcccttt ggttggtaaa     660
gattttaatg tggactcctt tgtaaatgct catgattttg attctttaga aagattagtt     720
gagtatatta tagaattgga ttcttcaaag gataaatatc tggaaatgtt ggaaaaacct     780
tggcttctcg ataagacata tttggattgg aaacaattgc tgttaaattt tattaataat     840
attatgatga atcatataa ggatgcgaag tatttggtta ttatggtca tgctggaaag      900
tatagaaatg aacaacgctt ttgggggaga tgtgaacgta aatttaaact tcaaagaatt     960
attgaatatt attctcaatt gtttgataga aaataa                               996
```

<210> SEQ ID NO 4
<211> LENGTH: 331
<212> TYPE: PRT
<213> ORGANISM: Bacteroides fragilis

<400> SEQUENCE: 4

```
Met Cys Asp Cys Leu Ser Ile Ile Leu Leu Val Lys Met Lys Lys Ile
1               5                   10                  15

Tyr Leu Lys Phe Val Asp Phe Trp Asp Gly Phe Asp Thr Ile Ser Asn
                20                  25                  30

Phe Ile Val Asp Ala Leu Ser Ile Gln Tyr Glu Val Val Leu Ser Asn
            35                  40                  45

Glu Pro Asp Tyr Leu Phe Tyr Ser Cys Phe Gly Thr Ser His Leu Glu
        50                  55                  60

Tyr Asp Cys Ile Lys Ile Met Phe Ile Gly Glu Asn Ile Val Pro Asp
65                  70                  75                  80

Phe Asn Val Cys Asp Tyr Ala Ile Gly Phe Asn Tyr Ile Asp Phe Gly
                85                  90                  95

Asp Arg Tyr Leu Arg Leu Pro Leu Tyr Ala Ile Tyr Asp Gly Phe Ser
            100                 105                 110

Asn Leu Gln Asn Lys Lys Ile Asp Val Asn Lys Ala Leu Asp Arg Lys
        115                 120                 125

Phe Cys Ser Ile Val Val Ser Asn Asn Lys Trp Ala Asp Pro Ile Arg
    130                 135                 140

Glu Thr Phe Phe Lys Leu Leu Ser Ser Tyr Lys Lys Val Asp Ser Gly
145                 150                 155                 160

Gly Arg Ala Trp Asn Asn Ile Gly Gly Pro Val Asp Asn Lys Leu Asp
                165                 170                 175

Phe Ile Ser Gln Tyr Lys Phe Asn Ile Ala Phe Glu Asn Ser Arg Val
            180                 185                 190
```

```
Leu Gly Tyr Thr Thr Glu Lys Ile Met Glu Pro Met Gln Val Asn Ser
            195                 200                 205

Ile Pro Val Tyr Trp Gly Asn Pro Leu Val Gly Lys Asp Phe Asn Val
    210                 215                 220

Asp Ser Phe Val Asn Ala His Asp Phe Asp Ser Leu Glu Arg Leu Val
225                 230                 235                 240

Glu Tyr Ile Ile Glu Leu Asp Ser Ser Lys Asp Lys Tyr Leu Glu Met
                245                 250                 255

Leu Glu Lys Pro Trp Leu Leu Asp Lys Thr Tyr Leu Asp Trp Lys Gln
            260                 265                 270

Leu Leu Leu Asn Phe Ile Asn Asn Ile Met Met Lys Ser Tyr Lys Asp
        275                 280                 285

Ala Lys Tyr Leu Val Asn Tyr Gly His Ala Gly Lys Tyr Arg Asn Glu
    290                 295                 300

Gln Arg Phe Trp Gly Arg Cys Glu Arg Lys Phe Lys Leu Gln Arg Ile
305                 310                 315                 320

Ile Glu Tyr Tyr Ser Gln Leu Phe Asp Arg Lys
                325                 330

<210> SEQ ID NO 5
<211> LENGTH: 891
<212> TYPE: DNA
<213> ORGANISM: Bacteroides fragilis

<400> SEQUENCE: 5
atggatatat tgattctttt ttataatacg atgtggggat ttccactcga gttccgaaag      60
gaagatttac ctgggggctg tgtgataacg actgatcgaa acctcattgc aaaggcggat     120
gctgtggttt tccatttgcc cgatttgcct tcggtgatgg aggatgaaat cgataagcgg     180
gaaggacagc tttgggtggg atggagtctg gaatgtgaag agaattatag ttggacgaag     240
gatcccgagt tcagagagag ttttgactta tggatgggtg tcatcagga ggatgatatt     300 gtgtatcctt attatggacc ggattatggg aagatgctgg ttacggcacg gagggaaaag     360
ccttataaga agaaggcatg tatgtttatt tcgagtgata tgaaccggag tcatcgacaa     420
gagtatctta aggaattgat gcagtatacc gacatcgatt cgtatgggaa actataccgt     480
aattgtgaat tacctgttga ggatcgggga cgggatacac ttcttagtgt gatcggggat     540
tatcagtttg tgataagttt tgagaatgcg atagggaagg attatgtgac agaaaagttt     600
ttcaatcctt tgttggccgg tactgttccg gtctatctgg gagctcccaa tattcgggaa     660
tttgctccgg gagaaaattg tttctggat atttgtactt cgattctcc cgagggagta     720 gccgctttta tgaatcaatg ctatgatgac gaggcattgt atgaacgttt ttatgcatgg     780
aggaaacggc ctttattatt gtcgtttaca aaaaagttag agcaagtccg gagcaatccg     840
ttaatcaggc tttgccaaaa aatacacgaa ctaaaattgg gagggatatg a             891

<210> SEQ ID NO 6
<211> LENGTH: 295
<212> TYPE: PRT
<213> ORGANISM: Bacteroides fragilis

<400> SEQUENCE: 6

Met Asp Ile Leu Ile Leu Phe Tyr Asn Thr Met Trp Gly Phe Pro Leu
1               5                   10                  15

Glu Phe Arg Lys Glu Asp Leu Pro Gly Gly Cys Val Ile Thr Thr Asp
            20                  25                  30
```

Arg Asn Leu Ile Ala Lys Ala Asp Ala Val Val Phe His Leu Pro Asp
             35                  40                  45

Leu Pro Ser Val Met Glu Asp Glu Ile Asp Lys Arg Glu Gly Gln Leu
 50                  55                  60

Trp Val Gly Trp Ser Leu Glu Cys Glu Glu Asn Tyr Ser Trp Thr Lys
 65                  70                  75                  80

Asp Pro Glu Phe Arg Glu Ser Phe Asp Leu Trp Met Gly Tyr His Gln
             85                  90                  95

Glu Asp Asp Ile Val Tyr Pro Tyr Gly Pro Asp Tyr Gly Lys Met
            100                 105                 110

Leu Val Thr Ala Arg Arg Glu Lys Pro Tyr Lys Lys Ala Cys Met
            115                 120                 125

Phe Ile Ser Ser Asp Met Asn Arg Ser His Arg Gln Glu Tyr Leu Lys
130                 135                 140

Glu Leu Met Gln Tyr Thr Asp Ile Asp Ser Tyr Gly Lys Leu Tyr Arg
145                 150                 155                 160

Asn Cys Glu Leu Pro Val Glu Asp Arg Gly Arg Asp Thr Leu Leu Ser
                165                 170                 175

Val Ile Gly Asp Tyr Gln Phe Val Ile Ser Phe Glu Asn Ala Ile Gly
                180                 185                 190

Lys Asp Tyr Val Thr Glu Lys Phe Phe Asn Pro Leu Leu Ala Gly Thr
                195                 200                 205

Val Pro Val Tyr Leu Gly Ala Pro Asn Ile Arg Glu Phe Ala Pro Gly
                210                 215                 220

Glu Asn Cys Phe Leu Asp Ile Cys Thr Phe Asp Ser Pro Glu Gly Val
225                 230                 235                 240

Ala Ala Phe Met Asn Gln Cys Tyr Asp Asp Glu Ala Leu Tyr Glu Arg
                245                 250                 255

Phe Tyr Ala Trp Arg Lys Arg Pro Leu Leu Leu Ser Phe Thr Lys Lys
                260                 265                 270

Leu Glu Gln Val Arg Ser Asn Pro Leu Ile Arg Leu Cys Gln Lys Ile
                275                 280                 285

His Glu Leu Lys Leu Gly Gly
                290                 295

<210> SEQ ID NO 7
<211> LENGTH: 46
<212> TYPE: DNA
<213> ORGANISM: Artificial
<220> FEATURE:
<223> OTHER INFORMATION: Primer

<400> SEQUENCE: 7
ggggacaagt ttgtacaaaa aagcaggctt cgaaggagat agaacc         46

<210> SEQ ID NO 8
<211> LENGTH: 33
<212> TYPE: DNA
<213> ORGANISM: Artificial
<220> FEATURE:
<223> OTHER INFORMATION: Primer

<400> SEQUENCE: 8
taggacccag ctttcttgta caaagtggtc ccc         33

<210> SEQ ID NO 9
<211> LENGTH: 92
<212> TYPE: DNA

<213> ORGANISM: Artificial
<220> FEATURE:
<223> OTHER INFORMATION: Primer

<400> SEQUENCE: 9
ggggacaagt tgtacaaaa aagcaggctt cgaaggagat acaaccatgg gccatcacca      60
tcatcaccac aaaacgctga aaattagctt tc                                   92

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
ggggaccact ttgtacaaga aagctgggtc                                      30

<210> SEQ ID NO 11
<211> LENGTH: 31
<212> TYPE: DNA
<213> ORGANISM: Artificial
<220> FEATURE:
<223> OTHER INFORMATION: Primer

<400> SEQUENCE: 11
ggggacaagt tgtacaaaa aagcaggctt c                                     31

<210> SEQ ID NO 12
<211> LENGTH: 30
<212> TYPE: DNA
<213> ORGANISM: Artificial
<220> FEATURE:
<223> OTHER INFORMATION: Primer

<400> SEQUENCE: 12
ggggaccact ttgtacaaga aagctgggtc                                      30

<210> SEQ ID NO 13
<211> LENGTH: 73
<212> TYPE: DNA
<213> ORGANISM: Artificial
<220> FEATURE:
<223> OTHER INFORMATION: Primer

<400> SEQUENCE: 13
ggggacaagt tgtacaaaa aagcaggctt cgaaggagat acaaccatgt gtgattgctt      60
gtctatcata ttg                                                        73

<210> SEQ ID NO 14
<211> LENGTH: 63
<212> TYPE: DNA
<213> ORGANISM: Artificial
<220> FEATURE:
<223> OTHER INFORMATION: Primer

<400> SEQUENCE: 14
ggggaccact ttgtacaaga aagctgggtc ttattttcta tcaaacaatt gagaataata    60
ttc                                                                   63

<210> SEQ ID NO 15
<211> LENGTH: 79
<212> TYPE: DNA
<213> ORGANISM: Artificial

<220> FEATURE:
<223> OTHER INFORMATION: Primer

<400> SEQUENCE: 15
ggggacaagt ttgtacaaaa aagcaggctt cgaaggagat acaaccatgg atatattgat    60 tctttttat aatacgatg    79

<210> SEQ ID NO 16
<211> LENGTH: 54
<212> TYPE: DNA
<213> ORGANISM: Artificial
<220> FEATURE:
<223> OTHER INFORMATION: Primer

<400> SEQUENCE: 16
ggggaccact ttgtacaaga aagctgggtc catatccctc ccaattttag ttcg    54

<210> SEQ ID NO 17
<211> LENGTH: 38
<212> TYPE: DNA
<213> ORGANISM: Artificial
<220> FEATURE:
<223> OTHER INFORMATION: Primer

<400> SEQUENCE: 17
agctagccat gggcaaaacg ctgaaaatta gctttctg    38

<210> SEQ ID NO 18
<211> LENGTH: 34
<212> TYPE: DNA
<213> ORGANISM: Artificial
<220> FEATURE:
<223> OTHER INFORMATION: Primer

<400> SEQUENCE: 18
agctagctgc agttagcgac gcaggcgatt tttc    34

<210> SEQ ID NO 19
<211> LENGTH: 37
<212> TYPE: DNA
<213> ORGANISM: Artificial
<220> FEATURE:
<223> OTHER INFORMATION: Primer

<400> SEQUENCE: 19
gatcaccatg ggctgtgatt gcttgtctat catattg    37

<210> SEQ ID NO 20
<211> LENGTH: 44
<212> TYPE: DNA
<213> ORGANISM: Artificial
<220> FEATURE:
<223> OTHER INFORMATION: Primer

<400> SEQUENCE: 20
gatcaggatc cttatttct atcaaacaat tgagaataat attc    44

<210> SEQ ID NO 21
<211> LENGTH: 43
<212> TYPE: DNA
<213> ORGANISM: Artificial
<220> FEATURE:
<223> OTHER INFORMATION: Primer

<400> SEQUENCE: 21

```
gatcaccatg gatatattga ttcttttta taatacgatg tgg                        43

<210> SEQ ID NO 22
<211> LENGTH: 38
<212> TYPE: DNA
<213> ORGANISM: Artificial
<220> FEATURE:
<223> OTHER INFORMATION: Primer

<400> SEQUENCE: 22
gatcagaatt ctcatatccc tcccaattt agttcgtg                              38
```

FUCOSYLTRANSFERASES AND THEIR APPLICATIONS

CROSS REFERENCE TO RELATED APPLICATIONS

This application is a continuation of international patent application PCT/EP2011/067538, filed on Oct. 7, 2011 designating the U.S., which international patent application has been published in English language and claims priority from European patent application EP 10 187 167.1, filed on Oct. 11, 2010. The entire contents of these priority applications are incorporated herein by reference

BACKGROUND OF THE INVENTION

The present invention relates to novel fucosyltransferases and their applications.

Many (glyco)proteins, (glyco)lipids or oligosaccharides require the presence of particular fucosylated structures, in order to exhibit a particular biological activity. E.g., many intercellular recognition mechanisms require a fucosylated oligosaccharide: e.g., in order to be bound by cell adhesion molecules, such as L-selectin, specific cell structures have to comprise fucosylated carbohydrates. Another example for fucosylated structures having a biological function are structures that form the AB0 blood group system. Furthermore, therapeutic (glyco)proteins represent the fastest growing class of pharmaceutical reagents, whereby their pharmacokinetic properties and stability are/is ascribed to their glycans.

Due to their complex nature and inherent chemical properties, the chemical synthesis of glycoconjugates is a major challenge and associated with substantial difficulties. Unlike proteins and nucleic acids, for which automated synthesizers are commercially available, glycans—and let alone glycoconjugates—cannot (yet) be synthesized using a general commercial system. Apart from the requirement to control stereochemistry, the formation of specific linkages remains difficult.

In view of the complexness associated with the chemical or the combined enzymatic/chemical synthesis of glycoconjugates, recent approaches have used glycosyltransferases to enzymatically synthesize (glyco)proteins and (glyco)lipids comprising oligosaccharide residues.

Fucosyltransferases, which belong to enzyme family of glycosyltransferases, are widely expressed in vertebrates, invertebrates, plants and bacteria. They catalyze the transfer of a fucose residue from a donor, generally guanosinediphosphate fucose (GDP-fucose) to an acceptor, which include oligosaccharides, (glyco)proteins and (glyco)lipids. The thus fucosylated acceptor substrates are involved in a variety of biological and pathological processes.

Several fucosyltransferases have been identified, e.g. in the bacteria *Helicobacter pylori, Escherichia coli, Salmonella enterica*, in mammals, *Caenorhabditis elegans* and *Schistosoma mansoni*, as well as in plants, whereby based on the site of fucose addition, fucosyltransferases are classified into alpha-1,2, alpha-1,3/4 and O-fucosyltransferases.

In mammals, GDP-Fucose is synthesized in the cytoplasm through de novo synthesis and salvage pathway. With the de novo synthesis, GDP-mannose is converted to GDP-fucose via two enzymes, whilst the salvage pathway utilizes the free cytosolic fucose as substrate. In the cell, GDP-fucose becomes concentrated in vesicles and is recognized by fucosyltransferases as a donor substrate.

Since the biological activity of many commercially important oligosaccharides, (glyco)proteins and (glyco)lipids depends upon the presence of particular fucose residues, there is a need in the state of the art to efficiently synthesize or produce glycoconjugates that have the desired oligosaccharide residue(s).

SUMMARY OF THE INVENTION

Thus, it is an object of the present invention to provide for tools and methods by means of which fucosylated substrates can be produced in an efficient, time- and cost saving way, which yields high amounts of the desired substrate.

According to the invention, this and other objects are solved, inter alia, by the provision of an isolated polynucleotide encoding a polypeptide with alpha-1,3 fucosyltransferase activity and comprising a sequence or consisting of a sequence selected from the group consisting of:
 a) SEQ ID Nos. 1, 3 or 5 of the attached sequence listing;
 b) a nucleic acid sequence complementary to SEQ ID Nos. 1, 3 or 5;
 c) nucleic acid sequences which hybridize under stringent conditions to the nucleic acid sequences defined in a) and b) or their complementary strands.

The polynucleotides according to the invention represent fucosyltransferases of the species *Akkermansia muciniphila* and *Bacteroides fragilis*, wherein the SEQ ID No. 1 displays the polynucleotide sequence of a newly identified fucosyltransferase of *Akkermansia muciniphila*, and wherein the SEQ ID Nos. 3 and 5 display polynucleotide sequences of two newly identified fucosyltransferases of *Bacteroides fragilis*.

The newly identified fucosyltransferases have surprising effects since by using them reactions can be performed which are not naturally occurring: Within the scope of the presenting invention it has been found that the above identified alpha-1,3 fucosyltransferases are able to use lactose as substrate and are able to produce fucosylated oligosaccharides, in particular 3-fucosyllactose. Up to date, none of the known alpha-1,3 fucosyltransferases isolated from bacteria has been shown to use lactose as a natural substrate for the production of fucosyllactose. Thus, the suitability of the newly identified fucosyltransferases to be used for producing fucosylated oligosaccharides is highly surprising, and, thus, their use represents an excellent tool to easily, efficiently and cost-saving produce, e.g., human milk oligosaccharides (HMOs), such as fucosyllactose. Today, more than 80 compounds, belonging to HMOs, have been structurally characterized; they represent a class of complex oligosaccharides that function as prebiotics. Additionally, the structural homology of HMO to epithelial epitopes accounts for protective properties against bacterial pathogens. Within the infant gastrointestinal tract, HMOs selectively nourish the growth of selected bacteria strains and are, thus, priming the development of a unique gut microbiota in breast milk-fed infants.

Since until now, the structural complexity of these oligosaccharides has hindered their synthetic production, the main source for HMOs is still human milk. Thus, there is a need for readily and easily obtainable HMOs, which can be provided by using the—surprisingly suitable—fucosyltransferases presented herein.

BRIEF DESCRIPTION OF THE DRAWINGS

Several embodiments of the invention are illustrated in the figures and explained in more detail in the following description. In the figures:

FIG. 5 shows the DNA sequence and amino acid sequence of gene amuc0760co (SEQ ID NO: 1) and protein Amuc0760co (SEQ ID NO: 2);

FIG. 6 shows the DNA sequence (SEQ ID NO: 3) and amino acid sequence (SEQ ID NO: 4) of gene fucT6 and protein FucT6.

FIG. 7 shows the DNA sequence (SEQ ID NO: 5) and amino acid sequence (SEQ ID NO: 6) of gene fucT7 and protein FucT7;

SEQUENCE LISTING

Figure 1:
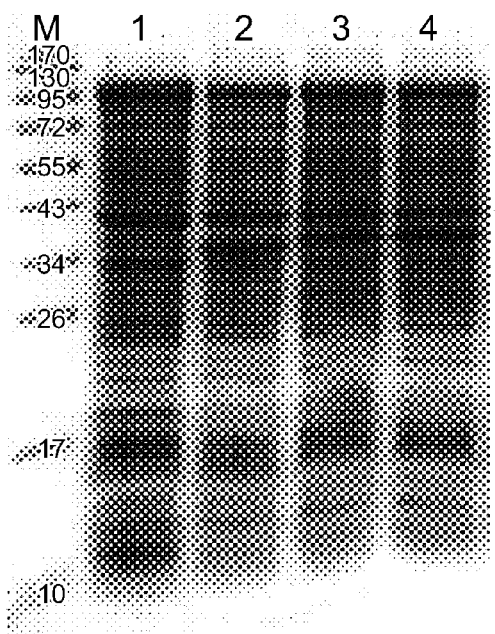
FIG. 1 shows the expression of Amuc0760co from pDEST14-amuc0760co in *Escherichia coli* JM109(DE3); 15 µg of soluble protein from crude extract were separated on 15% SDS-PAGE and stained with Coomassie Brilliant Blue.

The Sequence Listing is submitted as an ASCII text file [729]-90208-01_Sequence_Listing.txt, Apr. 10, 2013, 15.1 KB KB], which is incorporated by reference herein.

According to the present invention, the term "polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide (s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. Also, "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, lipid attachment, sulfation, gamma-carboxylation of glutamic acid residues, hydroxylation and ADP-ribosylation, selenoylation, transfer-RNA mediated addition of amino acids to proteins, such as arginylation, and ubiquitination. Polypeptides may be branched or cyclic, with or without branching. Cyclic, branched and branched circular polypeptides may result from post-translational natural processes and may be made by entirely synthetic methods, as well.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Similarly, a "synthetic" sequence, as the term is used herein, means any sequence that has been generated synthetically and not directly isolated from a natural source. "Recombinant" means genetically engineered DNA prepared by transplanting or splicing genes from one species into the cells of a host organism of a different species. Such DNA becomes part of the host's genetic makeup and is replicated.

The term "polynucleotide encoding a polypeptide" as used herein encompasses polynucleotides that include a sequence encoding a polypeptide of the invention, particularly an alpha-1,3-fucosyltransferase having the amino acid sequence as set forth in SEQ ID Nos. 2, 4, and 6. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

The terms "alpha-1,3-fucosyltranferase or fucosyltransferase" or a nucleic acid/polynucleotide encoding an "alpha-1,3-fucosyltranferase or fucosyltransferase" refer to a glycosyltransferase that catalyzes the transfer of fucose from a donor substrate, for example, GDP-fucose, to an acceptor molecule in an alpha-1,3-linkage. The acceptor molecule can be a carbohydrate, an oligosaccharide, a protein or (glyco)protein, or a lipid or (glyco)lipid, and can be, e.g., N-acetylglucosamine, N-acetyllactosamine, galactose, fucose, sialic acid, glucose, lactose or any combination thereof. Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a nucleic acid selected from SEQ ID Nos. 1, 3 or 5, or an amino acid sequence selected from SEQ ID Nos. 2, 4, or 6.

Additionally, the alpha-1,3-fucosyltransferase polypeptide may be altered by additions or deletions of peptide sequences in order to modify its activity. For example, polypeptide sequences may be fused to the alpha-1,3-fucosyltransferase polypeptide in order to effectuate additional enzymatic activity. Alternatively, amino acids may be deleted to remove or modify the activity of the protein. The protein may be modified to lack alpha-1,3-fucosyltransferase enzymatic activity but yet retain its structural three-dimensional structure. Such modification would be useful in the development of antibodies against alpha-1,3-fucosyltransferase polypeptide.

In addition, alpha-1,3-fucosyltransferase gene products may include proteins or polypeptides that represent functionally equivalent gene products. Such an equivalent alpha-1,3-fucosyltransferase gene product may contain deletions, additions or substitutions of amino acid residues within the amino acid sequence encoded by the alpha-1,3-fucosyltransferase gene sequences described above, but which results in a silent change, thus producing a functionally equivalent alpha-1,3-fucosyltransferase gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; planar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Within the context of this invention, "functionally equivalent", as used herein, refers to a polypeptide capable of exhibiting a substantially similar in vivo activity as the endogenous alpha-1,3-fucosyltransferase gene products encoded by the alpha-1,3-fucosyltransferase gene sequences described above, as judged by any of a number of criteria, including but not limited to antigenicity, i.e., the ability to bind to an anti-alpha-1,3-fucosyltransferase antibody, immunogenicity, i.e., the ability to generate an antibody which is capable of binding an alpha-1,3-fucosyltransferase protein or polypeptide, as well as enzymatic activity.

Included within the scope of the invention are alpha-1,3-fucosyltransferase proteins, polypeptides, and derivatives (including fragments) which are differentially modified during or after translation. Furthermore, non-classical amino acids or chemical amino acid analogs can be introduced as a substitution or addition into the alpha-1,3-fucosyltransferase polypeptide sequence.

The alpha-1,3-fucosyltransferase polypeptide may be produced by recombinant DNA technology using techniques well known in the art. Methods which are well known to those skilled in the art can be used to construct expression vectors containing alpha-1,3-fucosyltransferase coding sequences and appropriate transcriptional translational control signals. These methods include, for example, in vitro recombinant DNA techniques, synthetic techniques, and in vivo genetic recombination. See, for example, the techniques described in Sambrook et al., Molecular Cloning: A Laboratory Manual, 2nd Ed., Cold Spring Harbor Laboratory Press, Cold Spring Harbor, N.Y. (1989).

"Oligosaccharide" as the term is used herein and as generally understood in the state of the art, refers to a saccharide polymer containing a small number, typically three to ten, of simple sugars, i.e. monosaccharides.

According to another aspect of the invention, a vector is provided, containing a nucleic acid sequence as given above encoding a polypeptide with alpha-1,3-fucosyltransferase activity, wherein the nucleic acid sequence is operably linked to control sequences recognized by a host cell transformed with the vector. In a particularly preferred embodiment, the vector is an expression vector, and, according to another aspect of the invention, the vector can be present in the form of a plasmid, cosmid, phage, liposome, or virus.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., Basic Methods in Molecular Biology, (1986), and Sambrook et al., 1989, supra.

Thus, the polynucleotide according to the invention, may, e.g., be comprised in a vector which is to be stably transformed/transfected into host cells. In the vector, the polynucleotide of the invention is under control of an, e.g., inducible promoter, so that the expression of the gene/polynucleotide can be specifically targeted, and, if desired, the gene may be overexpressed in that way.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., see above.

Accordingly, the present invention also relates to an isolated polypeptide with alpha-1,3-fucosyltransferase activity consisting of an amino acid sequence selected from the group consisting of:
  (a) an amino acid sequence shown in SEQ ID NO: 2, 4 or 6;
  b) an amino acid sequence of an allelic variant of an amino acid sequence shown in SEQ ID No. 2, 4 or 6, wherein said allelic variant is encoded by a nucleic acid molecule that hybridizes under stringent conditions to the opposite strand of a nucleic acid molecule shown in SEQ ID Nos. 1, 3 or 5;
  c) an amino acid sequence of an ortholog of an amino acid sequence shown in SEQ ID No. 2, 4, or 6, wherein said ortholog is encoded by a nucleic acid molecule that hybridizes under stringent conditions to the opposite strand of a nucleic acid molecule shown in SEQ ID Nos. 1, 3, or 5; and
  (d) a fragment of an amino acid sequence shown in SEQ ID No. 2, 4, or 6, wherein said fragment comprises at least 10 contiguous amino acids, and wherein said fragment has an alpha-1,3-fucosyltransferase activity.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15 C lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Exemplary stringent hybridization conditions can be as following: 50% formamide, 5×SSC, and 1% SDS, incubating at 42 C, or, 5×SSC, 1% SDS, incubating at 65 C, with wash in 0.2×SSC, and 0.1% SDS at 65 C.

Also, the invention refers to a host cell containing a vector as defined above, and in particular a host cell which is selected from the group consisting of fungi including yeast, bacteria, insect, animal and plant cells. It is particularly preferred if the host cell is an *Escherichia coli* cell.

As used herein, the term "host cell" is presently defined as a cell which has been transformed or transfected, or is capable of transformation or transfection by an exogenous polynucleotide sequence, thus containing at least one sequence not naturally occurring in said host cell.

A variety of host-expression vector systems may be utilized to express the alpha-1,3-fucosyltransferase gene coding sequences of the invention. Such host-expression systems represent vehicles by which the coding sequences of interest may be produced and subsequently purified, but also represent cells which, when transformed or transfected with the appropriate nucleotide coding sequences, exhibit the alpha-1,3-fucosyltransferase gene product of the invention in situ.

A number of suitable expression systems and hosts can, e.g., be found in WO 98/55630, which deals with fucosyltransferases isolated from *Helicobacter pylori*, the publication of which is explicitly referred to herewith.

According to another aspect of the invention, the nucleic acid encoding the polypeptide with alpha-1,3-fucosyltransferase activity is adapted to the codon usage of the respective cell.

The invention relates to a method for producing fucosylated oligosaccharides, (glyco)proteins and (glyco)lipids, comprising the steps of:
  a. providing a polypeptide with alpha-1,3-fucosyltransferase activity according to the invention,
  b. contacting the polypeptide with alpha-1,3-fucosyltransferase activity of step a. with a mixture comprising a donor substrate comprising a fucose residue, and an acceptor substrate comprising a mono- or oligosaccharide, (glyco)protein or (glyco)lipid under conditions where the polypeptide catalyzes the transfer of a fucose residue from the donor substrate to the acceptor substrate, thereby producing a fucosylated oligosaccharide, (glyco)protein or (glyco)lipid.

According to the invention, the method for producing fucosylated oligosaccharides may be performed in a cell-free system or in a system containing cells. The substrates are allowed to react with the alpha-1,3-fucosyltransferase polypeptide for a sufficient time and under sufficient conditions to allow formation of the enzymatic product. It is to be understood, that these conditions will vary depending upon the amounts and purity of the substrate and enzyme, whether the system is a cell-free or cellular based system. These variables will be easily adjusted by those skilled in the art.

In cell-free systems, the polypeptide according to the invention, the acceptor substrate(s), donor substrate(s) and, as the case may be, other reaction mixture ingredients, including other glycosyltransferases and accessory enzymes are combined by admixture in an aqueous reaction medium. The enzymes can be utilized free in solution, or they can be bound or immobilized to a support such as a polymer and the substrates may be added to the support. The support may be, e.g., packed in a column.

Cell containing systems for the synthesis of fucosylated oligosaccharides may include recombinantly modified host cells.

Thus, the invention also relates to a method for producing fucosylated oligosaccharides, (glyco)proteins and (glyco)lipids, comprising the steps of:
   a. growing, under suitable nutrient conditions permissive for the production of the fucosylated oligosaccharide, (glyco)protein and/or (glyco)lipid, and permissive for the expression of a polypeptide with alpha-1,3-fucosyltransferase activity, a host cell as described above;
   b. providing, simultaneously or subsequently to step a., a donor substrate comprising a fucose residue and an acceptor substrate comprising an oligosaccharide, (glyco)protein or (glyco)lipid, so that the alpha-1,3-fucosyltransferase expressed in said host cell catalyzes the transfer of a fucose residue from the donor substrate to the acceptor substrate, thereby producing a fucosylated oligosaccharide, (glyco)protein or (glyco)lipid; and
   c. isolating said fucosylated oligosaccharide, (glyco)protein and/or (glyco)lipid from the host cell or the medium of its growth.

In the method according to the invention, the donor substrate may be GDP-fucose. It is particularly preferred if the donor substrate is GDP-fucose.

According to one aspect of the invention, the acceptor substrate is selected from N-acetylglucosamine, N-acetyllactosamine, galactose, fucose, sialic acid, glucose, lactose or any combination thereof. In particular, lactose is preferred as acceptor substrate.

The term "substrate", as used herein, means any material or combinations of different materials that may be acted upon by the polypeptide of the invention to give rise to fucosylated oligosaccharides, (glyco)proteins or (glyco)lipids.

The substrates are allowed to react with the alpha-1,3-fucosyltransferase polypeptide for a sufficient time and under sufficient conditions to allow formation of the enzymatic product. These conditions will vary depending upon the amounts and purity of the substrate and enzyme, whether the system is a cell-free or cellular based system. These variables will be easily adjusted by those skilled in the art.

According to one aspect of the method according to the invention, the donor substrate is provided in step b. by means of having it produced within the host cell. In doing so, an enzyme converting, e.g., fucose, which is to be added to the host cell, to GDP-fucose is simultaneously expressed in the host cell. This enzyme may be, e.g., a bifunctional fucose kinase/fucose-1-phosphate guanylyltransferase, like Fkp from *Bacteroides fragilis*, or the combination of one separate fucose kinase together with one separate fucose-1-phosphate guanylyltransferase like they are known from several species including *Homo sapiens, Sus scrofa* and *Rattus norvegicus*.

Alternatively, in step b., the donor substrate may be added to the culture medium/the host cells or be produced by the cells own metabolism.

In yet a further embodiment, the invention relates to a method comprising the following steps
   a) growing, host cells transformed or transfected to comprise a nucleic acid sequence selected from i) SEQ-ID-No. 1, 3, or 5 from the enclosed sequence listing, ii) a nucleic acid sequence complementary to SEQ ID No. 1, 3, or 5, and iii) nucleic acid sequences which hybridize under stringent conditions to the nucleic acid sequences defined in i) and ii) or their complementary strands, under suitable nutrient conditions so that the nucleic acid sequence selected from i), ii) and iii) are being expressed as a peptide having alpha-1,3-fucosyltransferase activity;
   b) providing, simultaneously or subsequently to step a., a donor substrate comprising a fucose residue and an acceptor substrate comprising an oligosaccharide, (glyco)protein or (glyco)lipid, so that the alpha-1,3-fucosyltransferase expressed in said host cell catalyzes the transfer of a fucose residue from the donor substrate to the acceptor substrate, thereby producing a fucosylated oligosaccharide, (glyco)protein or (glyco)lipid; and
   c) isolating said fucosylated oligosaccharide, (glyco)protein and/or (glyco)lipid from the host cell or the medium of its growth.

In the methods according to the invention, the peptide which is expressed in the host cell, displays alpha-1,3-fucosyltransferase activity and, thus, transfers a fucose residue from a donor, e.g. guanosine-diphosphate fucose (GDP-fucose), to an acceptor, which include oligosaccharides, (glyco)proteins and (glyco)lipids. In that way, the thus fucosylated acceptor substrate may be used as food additive, for the supplementation of baby food, or as either therapeutically or pharmaceutically active compound. With the novel methods, fucosylated products can easily and effectively be provided, without the need for complicated, time and cost consuming synthetic processes.

As used herein, the term "isolating" means harvesting, collecting or separating from the gene expression system the product produced by the alpha-1,3-fucosyltransferase according to the invention.

Accordingly, the invention also relates to the fucosylated oligosaccharide, (glyco)protein and/or (glyco)lipid obtained by the methods according to the invention, as well as to the use of a polynucleotide, the vector or the polypeptide as described above for the production of fucosylated oligosaccharides, (glyco)proteins and/or (glyco)lipids.

According to yet another embodiment, the production of said fucosylated oligosaccharide, (glyco)protein and/or (glyco)lipid is performed by means of a heterologous or homologous (over)expression of the polynucleotide encoding the alpha-1,3 fucosyltransferase.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described above and below are those well known and commonly employed in the art. Standard techniques are used for nucleic acid and peptide synthesis. Generally, enzymatic reactions and purification steps are performed according to the manufacturer's specifications.

The invention also covers fragments of the polynucleotide sequences disclosed therein.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

DESCRIPTION OF PREFERRED EMBODIMENTS

Example

Cloning of the Genes

Figure 3A:
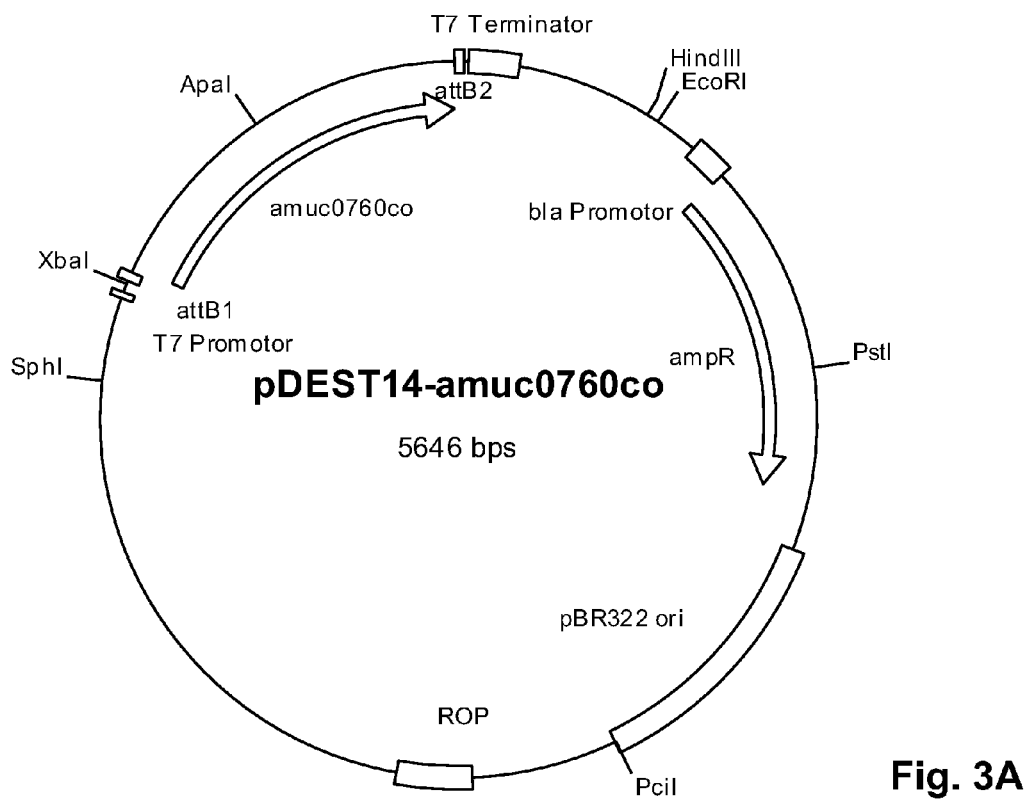
FIG. 3A-3C shows vector maps, including the vector map of pDEST14-amuc0760co, i.e. codon optimized gene amuc0760co coding the new alpha-1,3-fucosyltransferase Amuc0760co cloned into pDEST14 (Invitrogen) by Gateway-reaction (A); the vector map of pDEST14-fucT6, i.e. gene fucT6 from *Bacteroides fragilis* coding the new alpha-1,3-fucosyltransferase FucT6 cloned into pDEST14 (Invitrogen, Germany) by Gateway-reaction and (B); and the vector map of pDEST14-fucT7, i.e. gene fucT7 from *Bacteroides fragilis* coding the new alpha-1,3-fucosyltransferase FucT7 cloned into pDEST14 (Invitrogen, Germany) by Gateway-reaction (C).

The gene coding fucosyltransferase Amuc0760 was codon optimized and synthesized by GenScript, Piscataway, N.J. (USA). With two flanking sequences coding for attB-Sites for Gateway-Cloning (5'-sequence: GGGGA-CAAGTTTGTA-CAAAAAAGCAGGCTTCAAGGA-GATAGAACC (SEQ ID No. 7), 3'-sequence: TAGGAC-CCAGCTTTCTTGTACAAAGTGGTCCCC (SEQ ID No. 8)) it was cloned into pUC57 by GenScript. Gateway-transfer into vector pDEST14 (Invitrogen GmbH, Germany) (see FIG. 3A) was carried out according to the manual provided by the supplier (Invitrogen GmbH, Germany). The polynucleotide coding for N-terminally His-tagged Amuc0760co was amplified from pUC57-amuc0760co using primers GGGGACAAGTTTGTACAA- AAAAGCA-GGCTTCGAAGGAGATACAACCATGGGC-CATCACCATCATCACCACAAAACGCTGAAAATT-AGCTTTC (SEQ ID No. 9) and GGGGACCACTTTGTA-CAAGAAAGCTGGGTC (SEQ ID No. 10). The polynucleotide coding for C-terminally His-tagged amuc0760co was amplified from pUC57-amuc0760co using primers GGGGACAAGTTTGTACAAAAAAGC-AGGCTTC (SEQ ID No. 11) and GGGGACCACTTTGTA-CAAGAAAGCTGGGTC (SEQ ID No. 12).

Figure 3B:
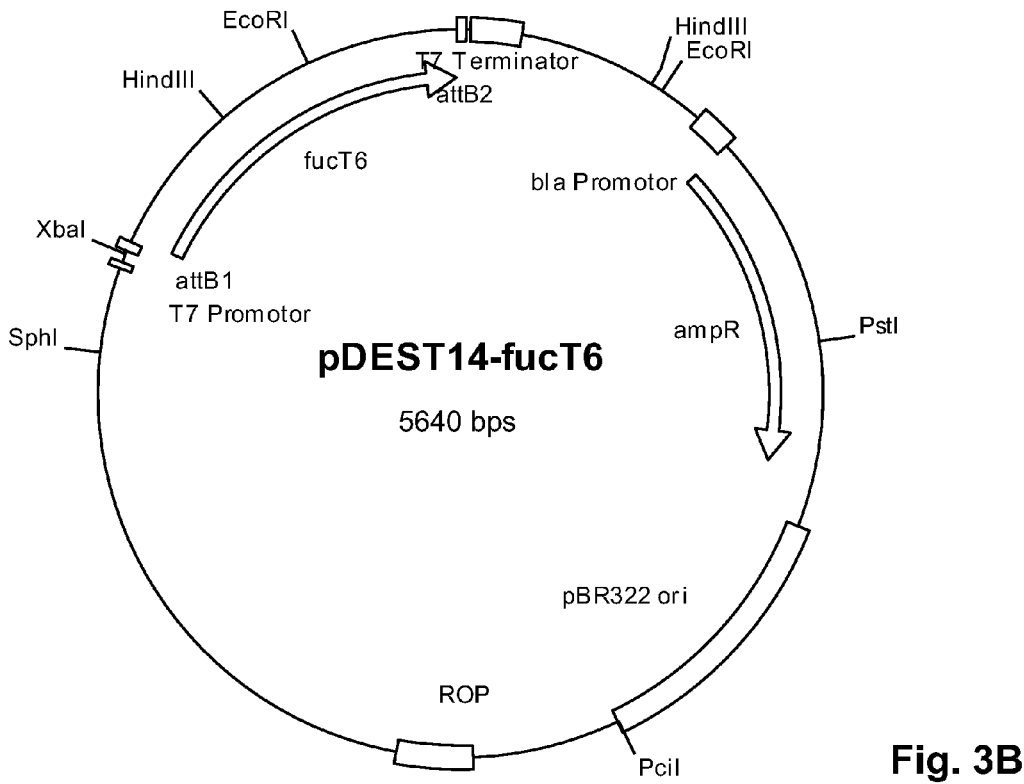
Figure 3C:
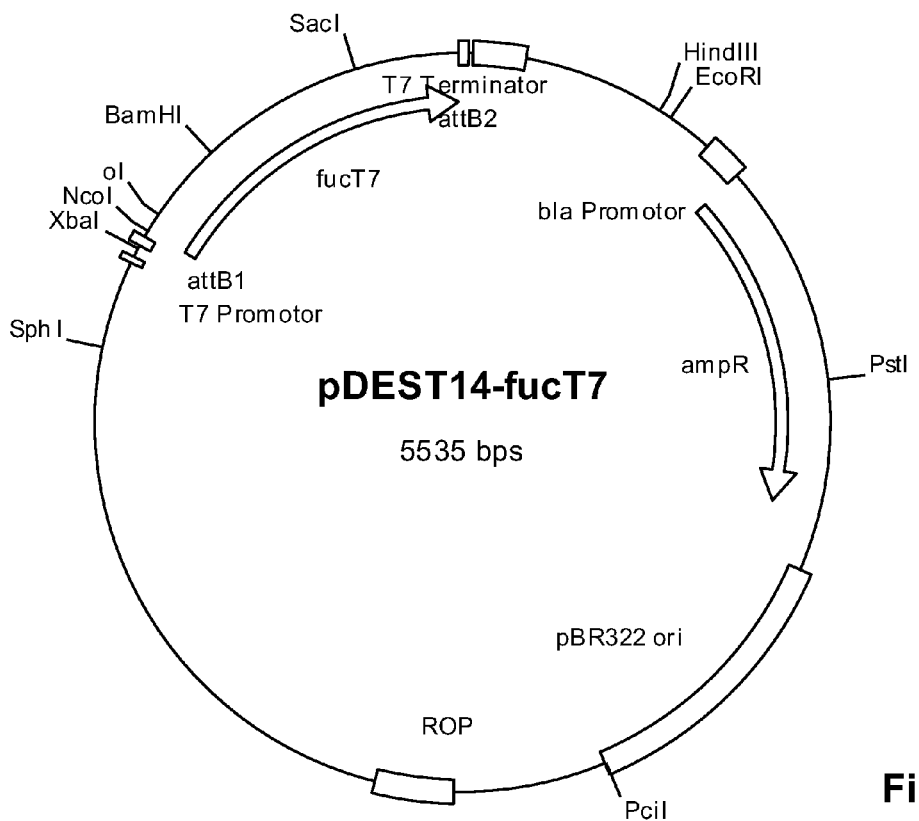

The genes coding for fucosyltransferases FucT6 and FucT7 were amplified from genomic DNA of Bacteroides fragilis NCTC 9343 with primers GGGGACAAGTTTG-TACAAAAAAGCAGGCTTCGAA-GGAGATACAACCATGTGTGATTGCTTGTCTATCAT-ATTG (SEQ ID No. 13)/GGGGACCACTTTGTA-CAAGAAAGCTGGGTCTTATTTTCTAT-CAAACAATT-GAGAATAATATTC (SEQ ID No. 14) and GGGGACAAGTTTGTACAAAAAAGCAGGCTTCAA-GGAGATACAACCATGGATATATTGATTCTTTTT-TATAATACGATG (SEQ ID No. 15)/GGGGACCACTTT-GTACAAGAAAGCTGGGTCCATATCCCTCCCAAT-TT-TAGTTCG (SEQ ID No. 16), respectively, and also cloned into pDEST14 using Gateway technology (Invitrogen GmbH, Germany) (see FIGS. 3B and 3C).

Expression of Fucosyltransferases

Figure 4A:
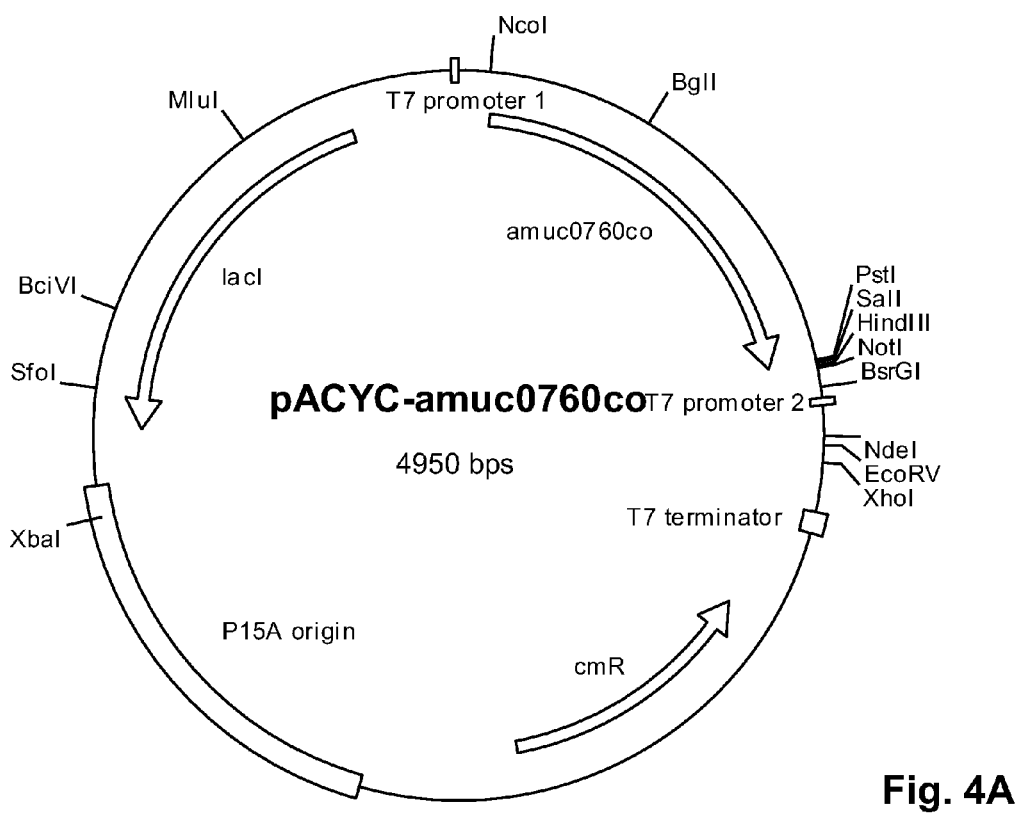
FIG. 4A-4C shows vector maps, including the vector map of pACYC-amuc0760co, i.e. codon optimized gene amuc0760co encoding the new alpha-1,3-fucosyltransferase Amuc0760co cloned into pACYCDuet-1 (Novagen via NcoI/PstI) (A); the vector map of pACYC-fucT6, i.e. codon optimized gene fucT6 from *Bacteroides fragilis* coding the new alpha-1,3-fucosyltransferase FucT6 cloned into pACYCDuet-1 (Novagen, UK) via NcoI/BamHI (B); and the vector map of pACYC-fucT7, i.e. codon optimized gene fucT7 from *Bacteroides fragilis* coding the new alpha-1,3-fucosyltransferase FucT7 cloned into pACYCDuet-1 (Novagen, UK) via NcoI/EcoRI (C).
Figure 4B:
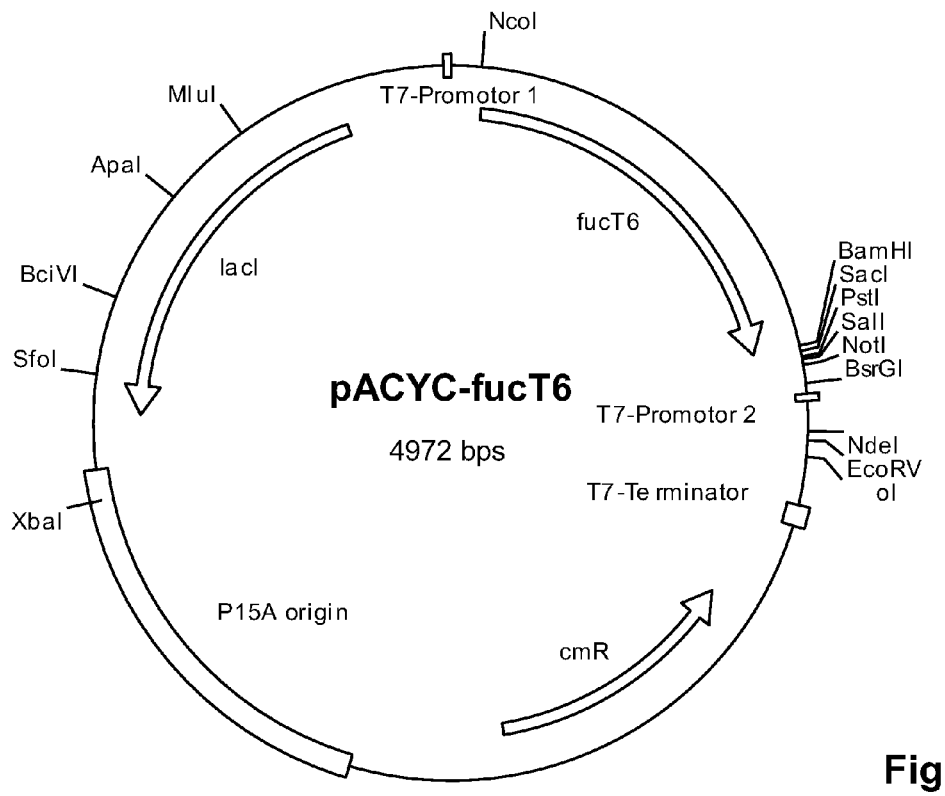
Figure 4C:
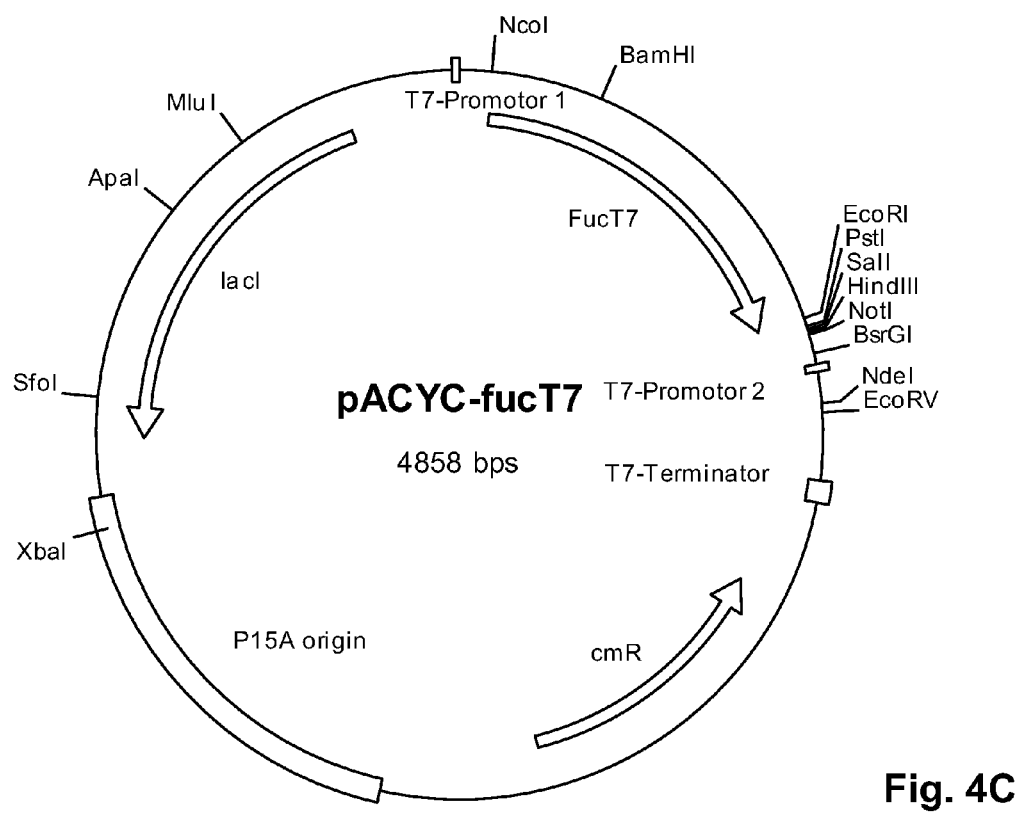

Genes amuc0760co, fucT6 and fucT7 were additionally cloned into expression vector pACYCDuet-1 (Novagen, UK). For cloning of amuc0760co via restriction with NcoI/PstI and subsequent ligation primers AGCTAG CCATGGGCAAAACGCTGAA-AATTAGCTTTCTG (SEQ ID No. 17) and AGCTAG CTGCAGTTAGCGACGCAGGCGAT-TTTTC (SEQ ID No. 18) were used (restriction sites are underlined) and the resulting product was called pACYC-amuc0760co (see FIG. 4A). fucT6 was cloned via NcoI/BamHI using primers GATCACCATGGGCTGTGATTGCTTGTCTATCATATTG (SEQ ID No. 19) and GATCAGGATCCT TATTTTCTAT-CAAACAATTGAGAATAATATTC (SEQ ID No. 20) (restriction sites underlined) resulting in pACYC-fucT6 (see FIG. 4B), and fucT7 was cloned via NcoI/EcoRI using primers GATCACCATGGATATATTGATTC TTTTT-TATAATACGA-TGTGG (SEQ ID No. 21) and GATCA GAATTCTCATATCCCTCCCAATTTTAGTTCGTG (SEQ ID No. 22) (restriction sites underlined) resulting in pACYC-fucT7 (see FIG. 4C).

E. coli strains JM109(DE3) or BL21(DE3) lacZ were transformed with the appropriate plasmids described above. 5 ml 2YT medium were inoculated by means of an inoculating loop and grown at 37° C. and 180 rpm over night. 400 ml 2YT were inoculated with 4 ml from the overnight culture and grown at 37° C. and 180 rpm until OD660 of 0.5 was reached. Expression was induced by addition of 0.1 mM IPTG and growth was continued at 28° C. and 180 rpm over night. Cells were harvested and resuspended in 4 v/w of either 50 mM Tris-HCl pH 7.5+5 mM $MgCl_2$ or, when used for purification via Ni Sepharose FF column (HisPrep FF 16/10, GE Healthcare, Sweden), in 4 v/w 20 mM Tris-HCl pH 7.5+500 mM NaCl+30 mM imidazole. Glass beads were added up to six times the weight of the cell pellet and the cell suspension was vortexed two times for 5 minutes, whereas in between the cell suspension was placed on ice for 5 minutes. After disruption cell debris was removed by centrifugation for 10 minutes at 15000×g. The resulting supernatant was used for analysis on SDS-PAGE or for purification via Ni Sepharose FF.

Detection Via Western Blot

Figure 2:
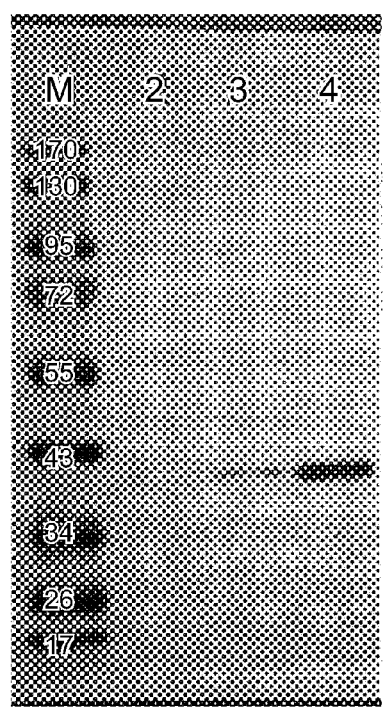
FIG. 2 shows the detection of His-tagged Amuc0760co via western blot.

His-tagged Amuc0760co was expressed as described above. From crude cell extract 10 mg of protein were separated on a 10% SDS gel. Proteins were blotted onto a PVDF membrane using a Mini Trans-Blot tank (Bio-Rad, Germany) according to the manual supplied by the manufacturer. His-tagged Amuc0760co was detected on the blot using His-Tag Antibody HRP Conjugate Kit (Novagen, UK) according to the instructions provided by the supplier (see FIG. 2).

Production of Fucosylated Compounds

Cells E. coli BL21(DE3) ΔlacZ pDEST14-fkp pCOLA-lacY-fucP were transformed with pACYC carrying the appropriate fucosyltransferase gene. Colonies were grown on 2YT plates with the appropriate antibiotics. 5 ml over night cultures (2YT with antibiotics) were grown of each strain and from this cultures 30 ml mineral medium each were inoculated to 1%. Cells were grown using glycerol as carbon source and at OD600=0.2 were induced with 0.1 mM IPTG and 20 mM lactose and 20 mM fucose were added. Production of 3-fucosyllactose was monitored by TLC and HPLC analysis. The comparison of the amount of 3-fucosyllactose (3-FL) produced by expression of FutA from Helicobacter pylori compared to the expression of Amuc0760co from Akkermansia muciniphila as well as FucT6 and FucT7 from Bacteroides fragilis is shown in the following table 1:

TABLE 1

Comparison of the amount of 3-fucosyllactose yield using alpha-1,3-fucosyltransferases FutA from Helicobacter pylori, Amuc0760co from Akkermansia muciniphila and FucT6 and FucT7 from Bacteroides fragilis

| Fucosyltransferase | Yield 3-FL [mM] |
|---|---|
| without (negative control) | 0 |
| FutA (Helicobacter pylori) | 3.83 |

TABLE 1-continued

Comparison of the amount of 3-fucosyllactose yield using alpha-1,3-fucosyltransferases FutA from *Helicobacter pylori*, Amuc0760co from *Akkermansia muciniphila* and FucT6 and FucT7 from *Bacteroides fragilis*

| Fucosyltransferase | Yield 3-FL [mM] |
|---|---|
| Amuc0760co (*Akkermansia muciniphila*) | 5.39 |
| FucT6 (*Bacteroides fragilis*) | 4.95 |
| FucT7 (*Bacteroides fragilis*) | 6.89 |

As can be seen from table 1, the amount of the fucosylated product 3-fucosyllactose was significantly higher when using the alpha-1,3-fucosyltransferases according to the invention, i.e. Amuc0760co from *Akkermansia muciniphila* and FucT6 and FucT7 from *Bacteroides fragilis*, compared to the alpha-1,3-fucosyltransferase FutA from *Helicobacter pylori*, which is state of the art.

Figure 8:
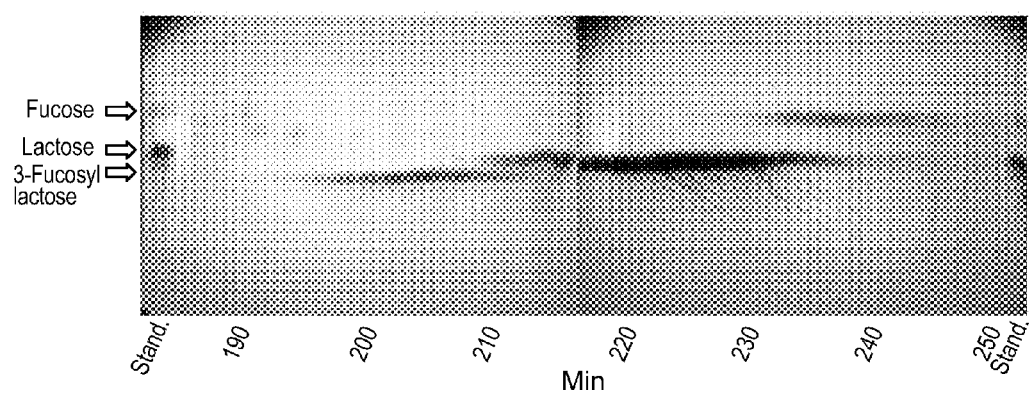
FIG. 8 shows the analysis of 3-fucosyllactose purification via BioGel P-2 gel permeation chromatography using thin layer chromatography with mobile phase butanol/acetone/acetic acid/water (35/35/7/23) and diphenylamine aniline staining solution (2% diphenylamine, 2% aniline, 10% phosphoric acid, in methanol)

Purification of the Fucosylation Product 3-fucosyllactose produced as described above was purified in several steps. First step was the purification by adsorption on activated charcoal. Culture supernatant from the production step was applied to a bed of activated charcoal. Flow-through was collected and analyzed, but no remaining 3-fucosyllactose was detected. For removal of unspecifically bound medium compounds such as e.g. salts and amino acids the bed was washed with distilled water (no 3-FL in flow-through). 3-FL and remaining lactose and fucose were then eluted with 96% ethanol. Ethanol was subsequently evaporated in a rotary evaporator and the residue filtrated via 10 kDa crossflow module (Microdyn Nadir, Germany). Remaining salts were removed by electrodialysation and thereafter endotoxins were removed by filtration using a cross-flow module (Pall, Germany). 3-FL was then separated from lactose and fucose in gram scale using gel permeation chromatography material Biogel P-2 (BioRad, Germany) packed into a 520 mm×428 mm glass column with frit. Purification of 3-FL was monitored by thin layer chromatography (see FIG. 8). Fractions containing only 3-fucosyllactose were pooled and freeze-dried.

Confirmation of the Identity of the Product

Figure 9A:
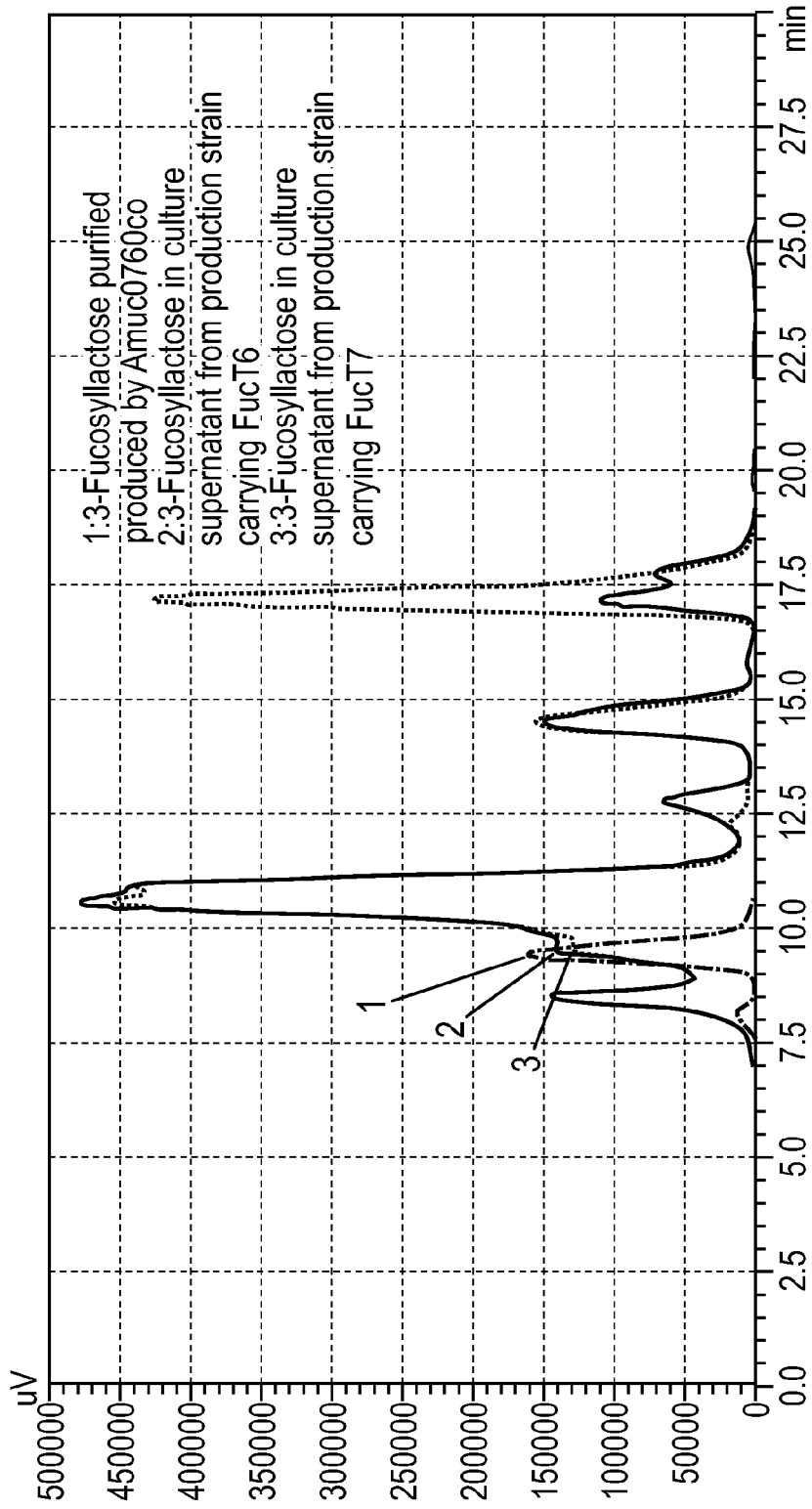
FIG. 9A-9B shows HPLC chromatograms. The HPLC chromatograms; separation by Phenomenex Rezex RCM Ca2+ column with water as eluent (0.6 ml/min for 30 minutes at 80° C.) and detection by refractive index detector (Shimadzu, Germany) (A); and the HPLC chromatogram; separation by Dionex CarboPac PA1 column with 50 mM NaOH as eluent (1 ml/min for 30 minutes at 30° C.) and detection by electrochemical detector DECADE II (Antec Leyden, Netherlands) (B).
Figure 9B:
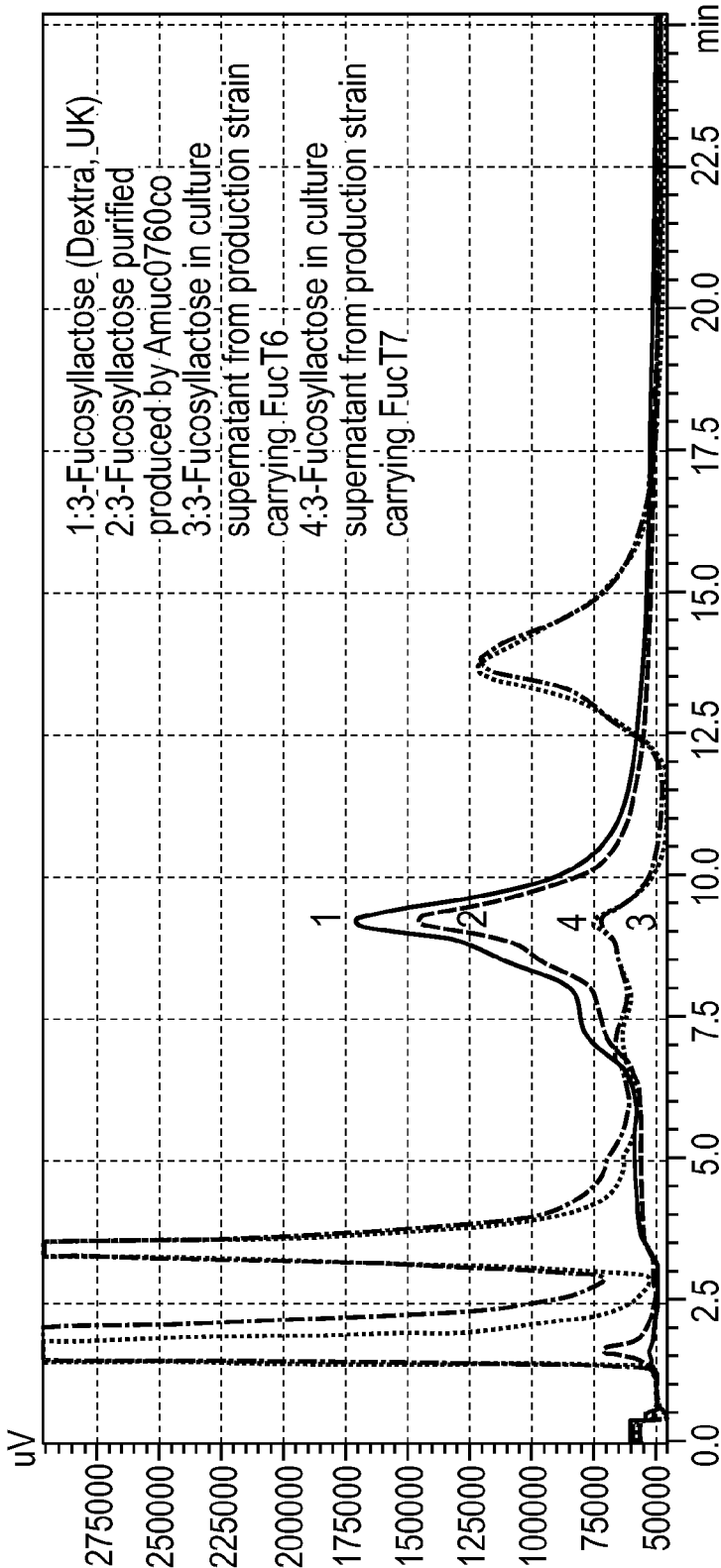

Purified 3-fucosyllactose produced using the fucosyltransferases presented in this invention was analyzed by 1H-NMR and mass spectrometry. The resulting spectra were consistent with the spectra expected for 3-FL. In addition to that different HPLC methods were applied to verify the identity of the resulting 3-FL. One method was the separation using Phenomenex Rezex RCM Ca2+ column with water as eluent (0.6 ml/min for 30 minutes at 80° C.) and detection by refractive index detector (Shimadzu, Germany) (see FIG. 9A). The other method was the separation via Dionex CarboPac PA1 column with 50 mM NaOH as eluent (1 ml/min for 35 minutes at 30° C.) and detection by electrochemical detector DECADE II (Antec Leyden, Netherlands) (see FIG. 9B).

What is claimed is:

1. A method for producing fucosylated oligosaccharides, the method comprising the steps of:
   a. providing a polypeptide with alpha-1,3-fucosyltransferase activity and with the ability to use lactose, or an oligosaccharide comprising a lactose residue, as acceptor substrate,
   wherein the polypeptide consists of the amino acid sequence set forth as one of SEQ ID NO. 2, SEQ ID NO: 4, SEQ ID NO: 6, an amino acid sequence at least 95% identical to the amino acid sequence set forth as SEQ ID NO. 2, an amino acid sequence at least 95% identical to the amino acid sequence set forth as SEQ ID NO: 4, or an amino acid sequence at least 95% identical to the amino acid sequence set forth as SEQ ID NO: 6; and
   b. contacting the polypeptide with alpha-1,3-fucosyltransferase activity of step a. with a mixture comprising a donor substrate comprising a fucose residue, and an acceptor substrate comprising lactose or an oligosaccharide comprising a lactose residue, under conditions where the polypeptide catalyzes the transfer of a fucose residue from the donor substrate to the acceptor substrate,
   thereby producing fucosylated oligosaccharides.

2. A method for producing fucosylated oligosaccharides, comprising the steps of:
   a. growing in vitro, a bacterial or fungal host cell comprising a vector, wherein the vector comprises a nucleic acid sequence encoding a polypeptide with alpha-1,3-fucosyltransferase activity and with the ability to use lactose, or an oligosaccharide comprising a lactose residue as an acceptor substrate, the nucleic acid sequence being operably linked to a control sequence, wherein the nucleic acid sequence is selected from the group consisting of the nucleic acid sequence set forth as SEQ ID NO: 1, the nucleic acid sequence set forth as SEQ ID NO: 3 the nucleic acid sequence set forth as SEQ ID NO: 5, a nucleic acid sequence complementary to the nucleic acid sequence set forth as SEQ ID NO: 1, a nucleic acid sequence complementary to the nucleic acid sequence set forth as SEQ ID NO: 3, and a nucleic acid sequence complementary to the nucleic acid sequence set forth as SEQ ID NO: 5;
   b. providing simultaneously or subsequently to step a, a donor substrate comprising a fucose residue and an acceptor substrate comprising lactose or an oligosaccharide comprising a lactose residue, in order for the alpha-1,3-fucosyltransferase polypeptide to catalyze the transfer of a fucose residue from the donor substrate to the acceptor substrate, thereby producing a fucosylated oligosaccharide, and
   c. isolating said fucosylated oligosaccharide from the host cell or a medium of its growth.

3. The method of claim 1, wherein the donor substrate is GDP-fucose.

4. The method of claim 2, wherein the donor substrate is GDP-fucose.

5. The method of claim 3, wherein the GDP-fucose is provided by an enzyme simultaneously expressed in the host cell or by the metabolism of the host cell.

6. The method of claim 4, wherein the GDP-fucose is provided by an enzyme simultaneously expressed in the host cell or by the metabolism of the host cell.

7. The fucosylated oligosaccharide obtained by the method of claim 1.

8. The fucosylated oligosaccharide obtained by the method of claim 2.

9. A method for producing a fucosyllactose using a bacterial or fungal host cell, comprising the steps of:
   a. growing, in vitro, a bacterial or fungal host cell transformed or transfected to express an exogenous polypeptide with alpha-1,3-fucosyltransferase activity and with the ability to use lactose as an acceptor substrate, wherein the polypeptide comprises the amino acid sequence set forth as SEQ ID NO. 2, the amino acid sequence set forth as SEQ ID NO: 4, the amino acid sequence set forth as SEQ ID NO: 6, an amino acid sequence at least 95% identical to the amino acid sequence set forth as SEQ ID NO. 2, an amino acid sequence at least 95% identical to the amino acid sequence set forth as SEQ ID NO: 4, or an amino acid sequence at least 95% identical to the amino acid sequence set forth as SEQ ID NO: 6; and
   i) an exogenous polypeptide with a bifunctional fucose-1-phosphate guanylyltransferase/fucose kinase activity or ii) both an exogenous polypeptide with fucose-l-phosphate guanylyltransferase activity and an exogenous polypeptide with fucose kinase activity;
   b. providing, simultaneously or subsequently to step a, a donor substrate comprising a fucose residue and an acceptor substrate, wherein the acceptor substrate is selected from a mono- or disaccharide or a combination thereof, wherein the alpha-1,3-fucosyltransferase polypeptide catalyzes the transfer of a fucose residue from the donor substrate to the acceptor substrate, thereby producing a fucosyllactose; and
   c. isolating the fucosyllactose from the host cell or a medium of its growth.

10. The method of claim 1, wherein the produced fucoslyated oligosaccharide is 3-fucosyllactose.

11. The method of claim 2, wherein the produced fucosylated oligosaccharide is 3-fucosyllactose.

12. The method of claim 9, wherein the exogenous polypeptide comprises the amino acid sequence set forth as SEQ ID NO. 2, SEQ ID NO: 4, or SEQ ID NO: 6.

13. The method of claim 9, wherein the bacterial or fungal host cell is transformed with a nucleic acid molecule encoding the exogenous polypeptide, and wherein the nucleic acid molecule comprises the nucleic acid sequence set forth as SEQ ID NO: 1, SEQ ID NO: 3, or SEQ ID NO: 5.

14. The method of claim 2, wherein the host cell is an *E. coli* cell or a fungal cell.

15. The method of claim 5, wherein the host cell is an *E. coli* cell or a fungal cell.

16. The method of claim 9, wherein the produced fucosyllactose is 3-fucosyllactose.

17. The method of claim 9, wherein the polypeptide consists of the amino acid sequence set forth as SEQ ID NO: 2, SEQ ID NO: 4 or SEQ ID NO: 6.

18. The method of claim 9, wherein the polypeptide consists of the amino acid sequence at least 95% identical to the amino acid sequence set forth as SEQ ID NO. 2, the amino acid sequence at least 95% identical to the amino acid sequence set forth as SEQ ID NO: 4, or the amino acid sequence at least 95% identical to the amino acid sequence set forth as SEQ ID NO: 6.

* * * * *